(12) United States Patent
Ustuner et al.

(10) Patent No.: US 7,887,486 B2
(45) Date of Patent: Feb. 15, 2011

(54) ADAPTIVE GRATING LOBE SUPPRESSION IN ULTRASOUND IMAGING

(75) Inventors: Kutay F. Ustuner, Mountain View, CA (US); Albert Gee, Los Altos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1007 days.

(21) Appl. No.: 11/724,526

(22) Filed: Mar. 14, 2007

(65) Prior Publication Data

US 2007/0173722 A1 Jul. 26, 2007

Related U.S. Application Data

(62) Division of application No. 10/627,290, filed on Jul. 25, 2003, now Pat. No. 7,207,942.

(51) Int. Cl.
*A61B 8/00* (2006.01)
(52) U.S. Cl. .................. 600/443; 600/437; 600/447; 600/455; 600/456; 600/458; 73/625; 73/626
(58) Field of Classification Search .................. 600/437, 600/443, 447, 455–456, 458; 73/625, 626
See application file for complete search history.

(56) References Cited

U.S. PATENT DOCUMENTS

| | | | |
|---|---|---|---|
| 4,179,683 A | 12/1979 | Hildebrand et al. | |
| 4,631,710 A | 12/1986 | Yamaguchi et al. | |
| 5,549,111 A | 8/1996 | Wright et al. | |
| 5,590,658 A | 1/1997 | Chiang et al. | |
| 6,135,971 A | 10/2000 | Hutchinson et al. | |
| 6,205,224 B1 | 3/2001 | Underbrink | |
| 6,283,919 B1 | 9/2001 | Roundhill et al. | |

(Continued)

FOREIGN PATENT DOCUMENTS

JP 02209135 A 8/1990

(Continued)

OTHER PUBLICATIONS

"Grating Lobe Reduction in Ultrasonic Synthetic Focusing," Electronics Letters; Jul. 4, 1991; vol. 27; No. 14; pp. 1225-1227.

(Continued)

*Primary Examiner*—Brian Casler
*Assistant Examiner*—Baisakhi Roy (57) ABSTRACT

Adaptive grating lobe suppression is provided. Received ultrasound data is measured, compared or otherwise processed to determine the presence of grating lobe energy. A further process is then altered as a function of the level of grating lobe energy. In one embodiment, the adaptive grating lobe suppression is implemented in the receive beamformer. Data representing a virtual element is formed as a normalized sum of data from adjacent sparse elements. The data from the adjacent elements is correlated to determine the presence of grating lobe energy as a function of the amount of shift associated with the peak correlation. A phase shift is applied to the data representing the virtual element where sufficient grating lobe energy is determined. In another embodiment, an amount of grating lobe energy is measured by comparing data from prior to a filter with filtered data. The filter is selected to isolate main lobe energy from grating lobe energy. A gain is modulated as a function of any detected grating lobe energy or filtered or unfiltered data is selected for further processing.

10 Claims, 3 Drawing Sheets

U.S. PATENT DOCUMENTS

| | | | |
|---|---|---|---|
| 6,368,276 B1* | 4/2002 | Bullis | 600/437 |
| 6,524,253 B1 | 2/2003 | Abend | |
| 6,527,723 B2 | 3/2003 | Ossmann et al. | |
| 6,658,141 B1 | 12/2003 | Jeong | |
| 6,682,483 B1 | 1/2004 | Abend et al. | |
| 7,207,942 B2* | 4/2007 | Ustuner et al. | 600/443 |
| 7,534,209 B2* | 5/2009 | Abend et al. | 600/454 |
| 2005/0033165 A1* | 2/2005 | Ustuner et al. | 600/437 |
| 2007/0173722 A1* | 7/2007 | Ustuner et al. | 600/443 |

OTHER PUBLICATIONS

Sowelam, S. et al "Sparse Periodic Transducer Arrays Using the Effective Aperture Concept" GE R&D Tech Rept 98CRD187, Dec. 1998.

* cited by examiner

FIG.6B
MAIN LOBE
DIRECTION

FIG.6C
GRATING LOBE
DIRECTION

US 7,887,486 B2

ADAPTIVE GRATING LOBE SUPPRESSION IN ULTRASOUND IMAGING

CROSS-REFERENCE TO RELATED APPLICATION

This application claims priority to and is a divisional of U.S. patent application Ser. No. 10/627,290, filed Jul. 25, 2003, now U.S. Pat. No. 7,207,941.

BACKGROUND

The present invention relates to adaptive grating lobe suppression. In particular, based on measurements of the object field, clutter from grating lobes is detected, and if present, reduced or removed.

Grating lobes are a significant source of clutter for laterally under-sampled arrays. The spacing between the array elements needs to be sufficiently small to avoid or at least limit the amount of lateral under sampling. But, if the number of beam former channels is limited, which is particularly the case for multi-dimensional arrays, smaller element spacing results in a smaller aperture. Smaller apertures provide less lateral resolution and signal-to-noise ratio. For example, a 64×64 two-dimensional array with half wavelength spacing, results in 4,096 elements. To maintain the half wavelength or even wavelength spacing, a large number of beam-forming channels are required. To reduce the number of beam-forming channels in alternative embodiments, the multi-dimensional array is sparsely sampled, such as providing coarsely spaced element transducers. For example, a 32×32 element array is provided with one wavelength spacing. However, sparse spacing of the elements results in increased grating lobes. Grating lobes result in tissue or other structure spaced away from a region of interest contributing to the signal at the region of interest (i.e., undesired clutter).

Various approaches have been suggested to increase the aperture size without sparse sampling, such as including beamformer electronics in the transducer to reduce the number of cables extending from the transducer to the ultrasound system. Time division multiplexing and sub-array beam forming are provided at the transducer. However, the sophisticated electronics in the transducer are expensive and may result in data degradation.

U.S. Pat. No. 5,549,111 discloses grating lobe reduction through variable frequency techniques. The imaging center frequency, such as the transmit and associated receive frequency, is reduced as a function of an increasing steering angle. This technique assumes reflectors within the grating lobe fields contribute clutter. However, no, few or low echogenic targets may exist in a grating lobe field so that a variable frequency is not needed.

Adaptive techniques have been provided for phase aberration correction. The delay and apodization profiles are altered as a function of the differences in speed of sound through different tissues along a main lobe transmission region. Using complex correlation processing, the location of a peak value is determined to identify the desired delay and apodization profiles. The transmit and receive scanning then accounts for differences in tissue structure as a function of scan line for the main lobe energy transmissions. This technique may not reduce grating lobes.

BRIEF SUMMARY

The present invention is defined by the following claims, and nothing in this second should be taken as a limitation on those claims. By way of introduction, methods and systems for adaptive grating lobe suppression are described. Received ultrasound data is measured, compared or otherwise processed to determine the presence of grating lobe energy. A further process is then altered as a function of the level of grating lobe energy. In one embodiment, the adaptive grating lobe suppression is implemented in the receive beamformer. Data representing a virtual element is formed as a normalized sum of data from adjacent sparse elements. The data from the adjacent elements is also correlated. The presence of grating lobe energy is detected by a shift of the correlation peak relative to the expected correlation peak location corresponding to energy from the main lobe. A phase shift is applied to the data representing the virtual element when a sufficient grating lobe energy is determined. Alternately, that element pair (actual and virtual) can be turned off when sufficient grating lobe energy is present. In another embodiment, an amount of grating lobe energy is measured by comparing data from prior to a filter with filtered data. The filter is selected to isolate main lobe energy from grating lobe energy. A gain is modulated as a function of any detected grating lobe energy or filtered or unfiltered data is selected for further processing. In the two embodiments, imaging compromises, such as smaller aperture or lower frequency, are made only if grating lobe clutter is present in the object field.

In a first aspect, a method for adaptive grating lobe suppression and ultrasound processing is provided. Ultrasound data is acquired. A grating lobe level is determined as a function of the ultrasound data. Processing is altered in response to the grating lobe level. In a second aspect, a system is provided for implementing the acts of the first paragraph. The system includes an ultrasound transducer and a processor.

In a third aspect, a method for adaptive grating lobe suppression in ultrasound processing is provided. A level of grating lobe energy is measured from received ultrasound data. Data processes are adapted to reduce the level of grating lobe energy in the received ultrasound data.

Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
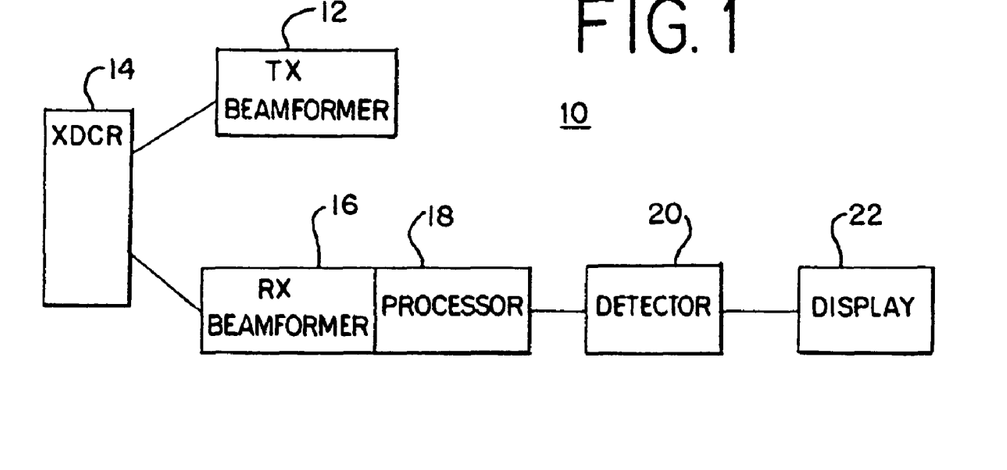
FIG. 1 is a block diagram of one embodiment of a system for grating lobe suppression.

FIG. 1 shows a block diagram of a system 10 for adaptive grating lobe suppression in ultrasound processing. The system 10 includes a transmit beamformer 12, a transducer 14, a receive beamformer 16, a processor 18, a detector 20 and a display 22. Additional different or fewer components may be provided. In one embodiment, the system 10 is a medical diagnostic ultrasound imaging system.

The transmit beamformer 12 comprises analog or digital components for generating a plurality of waveforms focused in a plane or along scan lines. The waveforms are generated at a desired center frequency for imaging. The bandwidth and center frequency of the transmit waveforms is selected such that the transducer 14 provides desired filtering or minimizes the amount of filtering by the transducer 14. The waveforms are provided to one or more elements of the transducer 14.

The transducer 14 is an array of piezoelectric or microelectro-mechanical elements. The elements are arrayed as a one-dimensional, 1.25D, 1.5D, 1.75D or 2D array. For example, a 2D array with 64×64 elements is provided. Other arrays with more or fewer elements in either azimuth or elevation dimensions are used in alternative embodiments. The elements are coarsely spaced for at least a band of frequencies at the upper band edge of the imaging spectrum. In yet other embodiments, the elements are spaced at half wavelength spacing but are sampled sparsely to reduce the number of required beamforming channels. The elements or sampling of elements may have random or even spacing.

The receive beamformer 16 includes amplifiers and delays in a plurality of channels connected by a multiplexer to the transducer 14. A summer sums the channels in the receive beamformer 16 to output in-phase/quadrature or radiofrequency ultrasound data. Any of analog and/or digital components are used in the receive beamformer 16. Any now known or later developed receive beamformers may be used.

The processor 18 is a digital signal processor, general processor, control processor, filter, digital circuitry, analog circuitry and combinations thereof. The processor 18 is either a part of the receive beamformer 16 or connects between the receive beamformer 16 and the detector 20. The processor 18 is connected with the transducer 14 through or as part of the receive beamformer 16. The processor 18 is operable to determine a level of grating lobe clutter in ultrasound data received from the transducer 14. The processor 18 is also operable to alter processing in response to the level of grating lobe clutter. For example, the processing of the processor 18, the receive beamformer 16, the detector 20, the transmit beamformer 12 or other component of an ultrasound system 10 is altered in response to the level of grating lobe clutter. The processor 18 alters the processing of other components by generating a control signal or information representing the detection of clutter or the level of clutter due to grating lobes.

In one embodiment of adaptive beamforming, the processor 18 correlates a range gated and focused signal from two different transducer elements. The presence of significant grating lobe energy is now detected when the correlation signal is larger at +/−1 carrier cycle relative to the correlation signal at 0. The signals from different transducer elements are averaged to represent a virtual element. The signal representing the virtual element is altered as a function of an amount of correlation or coherence. The processor 18 is operable to apply no or 180 degree shift to the signals representing the virtual element to suppress grating lobe energy. The signals representing the phased virtual element and one of the actual transducer element are then summed or beamformed as a channel pair. Alternately, this pair could be disabled from contributing to the beamformer output if significant grating lobe energy is present. The resulting beamformer output data may have suppressed or reduced grating lobe clutter.

In an adaptive filtering embodiment, ultrasound data in the receive beamformer 16 prior to summation or beamformed ultrasound data output by the receive beamformer 16 is filtered by a narrow bandwidth low frequency filter. The filter is adapted to isolate main lobe information, such as by reducing high frequency signals associated with grating lobes. By comparing the output of the filter with the input of the filter, the processor 18 provides an indication of the amount of grating lobe energy. Later processing is then altered as a function of determination. For example, a system gain applied to each sample varies as a function of the level of grating lobe energy. As another example, data is selected for subsequent processing as a function of the amount of grating lobe energy. Where a large amount of grating lobe energy is measured, the ultrasound data output by the filter with reduced grating lobe component is selected for further processing.

Figure 2:
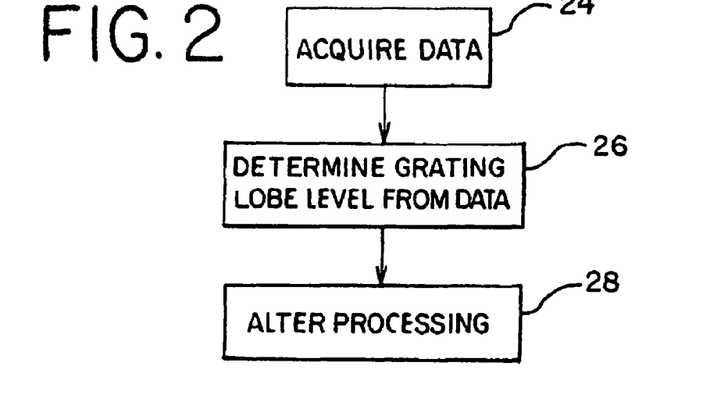
FIG. 2 is a flowchart diagram of one embodiment of a process for suppressing grating lobes.

FIG. 2 is a flowchart diagram of one embodiment of a method for adaptive grating lobe suppression and ultrasound processing. In act 24, ultrasound data is acquired. Ultrasound data includes channel data associated with individual channels of the receive beamformer 16 or beamformed data prior to detection. The level of grating lobe energy is determined from the data, so the determination is adaptive to the object field. Any of comparison, correlation, coherence, or other processes are used to identify energy associated with grating lobe clutter. The energy from grating lobes is isolated from other energy of the received data. In act 28, processing is altered in response to the determination of the grating lobe level. Any of various data processes are adapted to reduce the level of grating lobe energy in the receive ultrasound data or ultrasound data used for further processing.

The processor 18 adaptively reduces or eliminates grating lobes in the ultrasound data and resulting imaging signals based on a measure of the grating lobe energy. As a result, the design requirements for element spacing, imaging frequency and maximum steering angle are relaxed. Spacing, imaging frequency and maximum steering angle are typically chosen based on a worse case clinical situation, such as to avoid grating lobe clutter from the diaphragm in cardiology or from the fetus skull in obstetrics. Fewer array elements and system channels for a given imaging frequency and larger aperture size are made available; higher imaging frequencies, particularly for steered lines for a given element spacing are possible; or the maximum steering angle for a given imaging frequency and element spacing is increased. Combinations of these three features or other features of grating lobe suppression may be used for ultrasound imaging. Higher imaging frequencies and/or larger aperture sizes may allow for better lateral resolution. The use of fewer elements and system channels may allow for lower cost three-dimensional imaging with two-dimensional arrays. Increasing the maximum steering angle may allow for scanning a greater field of view.

Figure 3:
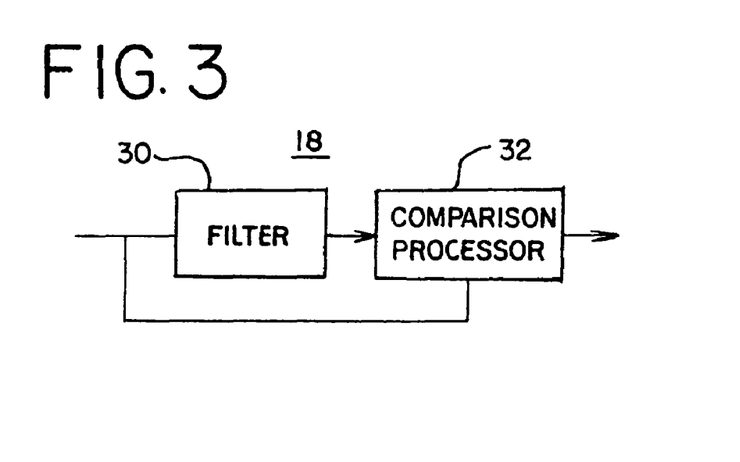
FIG. 3 is a block diagram of an adaptive filtering system for suppressing grating lobes.
Figure 4:
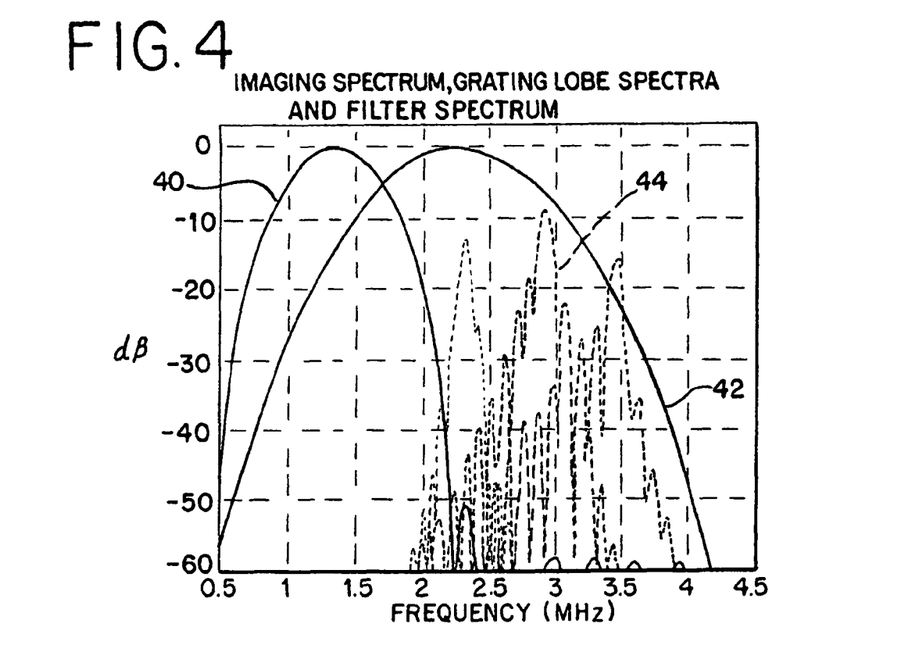
FIG. 4 is a graphical representation of spectra associated with adaptive filtering for grating lobe suppression.
Figure 5:
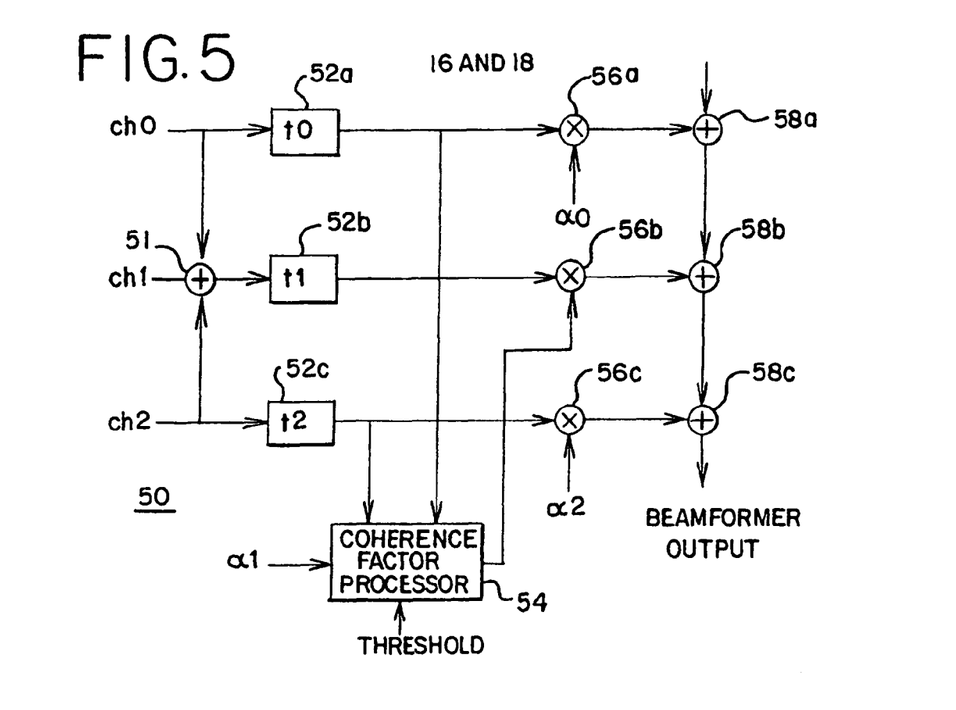
FIG. 5 is a block diagram of one embodiment of an adaptive beamforming system for grating lobe suppression.

FIGS. 3 through 6 represent two general embodiments for adaptive suppression of grating lobe energy. FIG. 3 represents a filter system for adaptively suppressing grating lobe energy. FIG. 5 represents an adaptive receive beamforming system for suppressing grating lobe energy. The systems of FIGS. 3 and 5 are used together or only one of the systems of FIG. 3 or 5 is used in the system 10. By suppressing grating lobe energy, a greater element spacing may be used for imaging. For three- or four-dimensional imaging, an increased separation of transducer elements allows for a lesser increase in beamforming channels. Since the grating lobe energy is suppressed, the additional clutter due to the sparse sampling is minimized or avoided.

FIG. 3 shows the processor 18 configured for adaptive filtering for grating lobe suppression. A grating lobe filter 30 outputs filtered ultrasound data or images with reduced or no grating lobe energy. A comparison processor 32 determines an amount of grating lobe energy in the ultrasound data as a function of the input and output of the grating lobe filter 30. Grating lobe clutter is then reduced using gain modulation or a weighed combination of the input and output of the grating lobe filter 30.

The grating lobe filter 30 is a digital filter, analog filter, digital signal processor, application specific integrated circuit, general processor or other now known or later developed filter. The filtering is done in time or frequency domain. In one embodiment, the grating lobe filter 30 is implemented with a processor that also implements the comparison processor 32, such that the grating lobe filter 30 and comparison processor 32 are a single device. The grating lobe filter 30 is a temporal, i.e., axial or range filter. The grating lobe filter 30 implements a finite impulse response filter providing band pass filtering of baseband, intermediate frequency or radiofrequency data. In one embodiment, the grating lobe filter 30 includes 8 to 16 taps, but longer or shorter filters may be provided as a function of the sampling rate of the complex or radiofrequency data and the bandwidth of the filter input. Different types of filters, types of band passes or other characteristics may be used.

The ultrasound data received is filtered prior to any amplitude detection. In one embodiment for temporally filtering, the grating lobe filter 30 is positioned after delays of the receive beamformer 16 and prior to channel summation. A plurality of grating lobe filters 30 operate in parallel or a reduced number of grating lobe filters operate in an interleaved manner to filter channel data prior to completion of beamformation. Apodization is applied prior to or after the filtering. By providing the adaptive grating lobe filter 30 in the receive channels prior to summation, a filter may adapt on a channel dependent basis. For those array elements that have a larger angle to the focal point, the receive data more likely includes grating lobe clutter. As a result, grating lobe energy is suppressed in the channels where needed but the larger bandwidth is used for other channels. The center frequency, a bandwidth, thresholds or combinations thereof may be varied from channel to channel to optimize the grating lobe detection.

In an alternative embodiment, a single grating lobe filter 30 is provided after the delay and sum to filter beamformed data output. By filtering the beamformed data, the grating lobe 30 acts as an axial or range filter.

The grating lobe filter 30 has a lower center frequency than is associated with the received ultrasound data. For example, FIG. 4 shows an imaging spectrum 42 where the ultrasound data has a center frequency around 2.3 MHz and a 10 dB bandwidth of about 1.5 MHz. The spectrum 40 of the grating lobe filter 30 is selected to provide a narrow bandwidth, bandpass filter, such as centered at about 1.4 MHz and having a 10 dB bandwidth of about 1 MHz. The imaging spectrum 42 and filter spectrum 40 may have wider or narrower bandwidths and different center frequencies. In the embodiment shown in FIG. 4, the center frequency of the grating lobe filter spectrum 40 is selected to be lower than the center frequency of the imaging spectrum 42 and at around −9 to −15 dB down on the imaging spectrum 42. The lower the center frequency the stronger the grating lobe suppression. But as the center frequency of the filter goes down, so does the signal to noise ratio, the lateral resolution and axial resolution of the filter output. The filtering spectrum 40 is selected as a function of various imaging parameters, including the received data center frequency or imaging frequency and known transducer 14 and system bandwidths. In alternative embodiments, the filter spectrum 40 is selected as a function of measured characteristics of the imaging spectrum 42. In yet other alternative embodiments, the filtering spectrum 40 and associated filtering parameters are fixed or only selected in response to the type of imaging application.

Since grating lobes are typically higher frequency signals, the lower frequency, narrow band filter spectrum 40 reduces energy from grating lobes, such as represented by the grating lobe spectrum 44. In one embodiment, the bandwidth of the filter spectrum 40 is selected to filter out one-half to one-third of the imaging frequency band, but other amounts maybe filtered. The ultrasound data input to the grating lobe filter 30 may potentially be cluttered by echoes from scatters located within the grating lobe fields. The output of the grating lobe filter 30 provides a signal that is freer of grating lobe clutter. As a result of the filtering, the filter output has lower axial and lateral resolution than the filter input.

The comparison processor 32 determines a grating lobe level as a function of the filter input and filter output. The comparison processor 32 is an application specific integrated circuit, digital signal processor, control processor, general processor, analog circuit, digital circuit, a look-up table, combinations thereof or other now known or later developed processing device. The comparison processor 32 compares received ultrasound data with filtered ultrasound data responsive to the grating lobe filter 30. Since the grating lobe filter 30 reduces the amount of grating lobe energy, a comparison indicates the level or amount of grating lobe energy in the received ultrasound data prior to filtering. In alternative embodiments, the grating lobe filter 30 filters out desired main lobe information while maintaining more grating lobe energy, such as filtering with a narrow band higher frequency than the center frequency of the imaging spectra. In either case, one of a difference or ratio of the filter input and filter output is performed by the comparison processor 32. For example, the grating lobe measure, GLM (X, N) is equal to a function of the absolute value of the filter input energy as a function of a two- or three-dimensional spatial index and frame, subtracted from an absolute value of the filtered energy output also as a function of the spatial index and frame index. As another example, the grating lobe measure is a function of the energy ratio of the filter input and output which vary as a function of the spatial index in two- or three-dimensional space and the frame number or time. Other linear or non-linear combinations of the received ultrasound data and output filter ultrasound data are used in alternative embodiments.

The difference between or the ratio of the signal energy over the full imaging spectrum and the signal energy over the low end of the imaging spectrum provides a measure of the grating lobe clutter. The higher the difference or ratio, the higher the grating lobe clutter. For the comparison, the comparison processor 32 calculates an energy, such as the sum of the square of the signal magnitude over a range gate time period for the ultrasound data from prior to and after the grating lobe filter 30. The sum of the magnitude or other characteristics of the ultrasound data is used in alternative embodiments.

In response to the output of the comparison processor 32 or as implemented by the comparison processor 32, one or more processes of the system 10 are altered or adapted based on the amount or level of grating lobe energy. In one embodiment, a gain is modulated as a function of the comparison. Any of various modulation functions may be used, including a binary decision to pass data at the system gain or set the gain to zero. In an alternative modulation function, the gain is adjusted over a plurality of possible values as a function of a plurality of different levels of grating lobe clutter.

Any of various system gains are modulated as a function of the grating lobe level. System gains include gains applied before and after the detector 20. For example, a gain applied for each channel in the receive beamformer to implement apodization is modulated based on the amount of grating lobe in the respective channel signal. In one embodiment, the gain is reduced in response to a sufficiently large or increasingly large amount of grating lobe energy. For example, dark or black pixels are generated by reducing the system gain applied to beamformed data for locations associated with a sufficiently large grating lobe level. With the modulated gain being after beamformation, the modulation may result in undesired dark spots in tissue structure. A less drastic change in the gain may avoid undesired dark spots but also reduce grating lobe clutter suppression.

To avoid dark spots in tissue structure, processing is adapted to select one of the received ultrasound data input to the grating lobe filter 30, the filtered ultrasound data output or combinations thereof as a function of the comparison. The selected data is used for imaging in one embodiment, the comparison processor 32 outputs a weighted summation of the filter input and output. The weights are a function of the grating lobe level. In one embodiment, a weight is calculated as the absolute value of the magnitude of the filter input minus the absolute value of the magnitude of the filter output. The filter coefficients in this case are scaled so that the filter has unity incoherent gain. Where the input magnitude is larger than the output magnitude, the filter output is passed for subsequent detection in imaging. Otherwise, the filter input is selected and passed for subsequent detection and imaging. In this embodiment, the weights are either (1) a one value for the filter output and zero value for the filter input or (2) a one for the filter input and a zero for the filter output. Other functions for determining the weight may be used, such as requiring a greater or lesser amount of grating lobe clutter for selecting between using the input data or output data masks for any pixel location. The selection is made on a pixel-by-pixel basis, resulting in a mask of locations associated with received ultrasound data without filtering by the grating lobe filter 30 and other locations associated with ultrasound data output by the grating lobe filter 30. In alternative embodiments, linear or nonlinear varying weights are applied, resulting in a selected or output ultrasound data that is a combination of both filtered and unfiltered ultrasound data.

By either replacing the received ultrasound data with filtered ultrasound data or by using a weighted combination, an adaptive imaging center frequency and/or adaptive bandwidth processes is provided for suppressing grating lobes. Where grating lobe energy is detected, a narrower band lower frequency signal is output. By selectively decreasing the bandwidth and center frequency, resulting image content is maximized while reducing grating lobe clutter. The resulting image is a function of the weighted summation, selection, or other process adaptively varied as a function of the grating lobe level.

In addition or as an alternative adaptive process, a grating lobe level measured for a previous ultrasound line or frame of ultrasound data is used to vary transmit and receive filters and apodization for subsequent ultrasound lines or frames. For example, an aperture size is reduced to decrease grating lobe levels. Alternatively, the shape of the aperture or the apodization applied is adaptively changed to provide less emphasis on channels associated with greater angles to the focal point. A transmit filter may be applied to transmit waveforms for edge elements of the aperture or the characteristics of the transmit filter vary as a function of a previous amount of grating lobe clutter.

FIG. 5 shows a block diagram of one embodiment of the receive beamformer 16 with the processor 18 included for adaptive beamformation to suppress grating lobe clutter. Grating lobe energy is adaptively rejected in beamforming as a function of the object field been scanned. Grating lobe artifacts are suppressed on a per element, per range sample, and/or per line basis. Signals from two different transducer elements are correlated, and a phase shift is adapted as a function of the location of the correlation peak. The phase shift is applied to data representing a virtual element interpolated from data for two actual elements. The signals representing the virtual element are delayed, phased, apodized and summed along with the data from actual elements. For receive signals principally from the grating lobe direction, the beamformer forms the data representing the virtual element to cancel the energy, such as by adjusting a phase by 180 degrees. If the signal is predominantly from the main lobe direction, the phase of the data representing the virtual element is the same as the phase of the other elements, enhancing the main lobe energy upon beamformation.

The adaptive receive beamformer 50 includes at least two channels connected to actual transducer elements (e.g. channel 0 and 2) and a virtual channel (e.g. channel 1). A beamform delay 52A, 52B and 52C, including a time delay and/or phase shift is implemented for each of the channels. In alternative embodiments, the delays 52A and 52C are provided prior to the summer 51. As a result, the delay 52B is not used, but may be used in alternative embodiments. The summer 51 sums the signals from the actual elements, such as adjacent real elements. The sum signal is normalized and the result represents the virtual element of channel 1. The multipliers 56A, 56B and 56C implement apodization or gain applied within the beamformer 50. The summers 58A and 58B sum the channel pair formed by a real element (channel 0) and a virtual element (channel 1). Summer 58C sum the output of the previous channel pair with the outputs of the adjacent channel pair formed by real channel 2 and virtual channel 3 (not shown). As shown, separate summers are provided for each of the channels to form a cascade sum. In alternative embodiments, a single summer 58 that sums three or more channel inputs is provided. While two actual channels and one virtual channel are shown in FIG. 5, additional real channels and/or virtual channels are provided, such as to implement 128 effective element array using 64 actual elements, or 128 by 128 effective element 2-D array using 64 by 64 actual elements or other number of sparsely spaced elements and 64 or other number of virtual elements. Channel 0 together with channel 1 represent a channel pair. Additional channel pairs (e.g., real channel 2 and virtual channel 3) are repeated. Other combinations of two or more channels may be used.

The coherence factor processor 54 is a digital signal processor, control processor, general processor, application specific integrated circuit, analog device, digital device, combinations thereof in any now known or later developed processor implemented in the beamformer 16. In one embodiment, the coherence factor processor 54 addresses a buffer in the receive beamformer 16 to acquire the ultrasound data. In one embodiment, the coherence factor processor 54 comprises a control processor with access to various channels in the receive beamformer 16. The coherence factor processor distinguishes between the relative energy coming from the grating lobe direction versus the main lobe direction. In one embodiment the coherence factor is defined as $Rxy(t)/(sqrt(Rxx(0).*Ryy(0)))$, where $Rxx(t)$=autocorrelation of channel 0, Ryy(t)=autocorrelation of channel 1, and Rxy(t)=cross correlation of channel 0 and channel 1. The apodization weight applied by the channel 1 multiplier 56B and output by the coherence factor processor 54 is a function of an apodization appropriate for the virtual element and a threshold selected to distinguish between signals associated with grating lobe energy and signals associated with main lobe energy. In another embodiment, the coherence factor processor multiples channel 0 and channel 1 by 0 if high level of grating lobe energy is detected. This effectively disables that channel pair from contributing to the beamformer output.

Figure 6A:
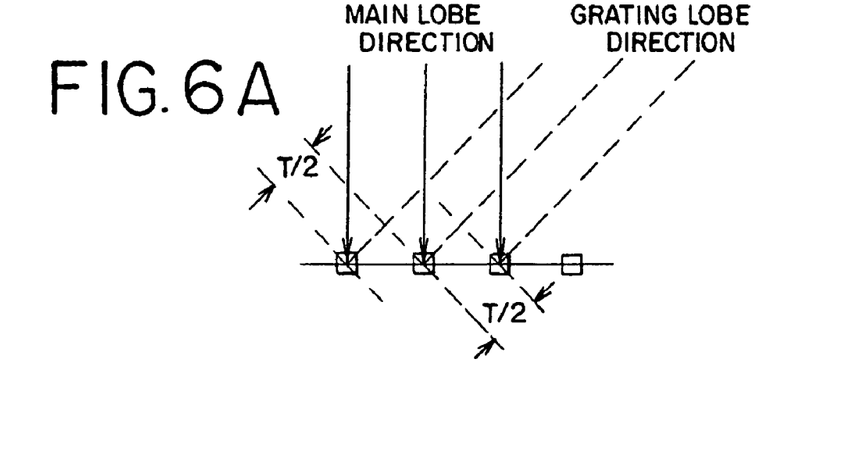
FIGS. 6A-6C show graphical representations of an adaptive beamforming process of one embodiment of grating lobe suppression.

FIG. 6A represents the differences in channels of information received from a main lobe direction and grating lobe direction. The grating lobe direction is shown as at a 45 degree angle to the main lobe direction. Grating lobe information is offset from the main lobe energy by half of a period for fully sampled arrays and by a full period for under sampled arrays. For example, for fully sampled arrays having both real channels 0 and 1, the energy from the main lobe direction would add constructively while the energy from the grating lobe direction would add destructively. For under sampled arrays having only real channels 0 and 2, energy from both main lobe and grating lobe add constructively. Other phasing offsets may be provided.

Figure 6B:
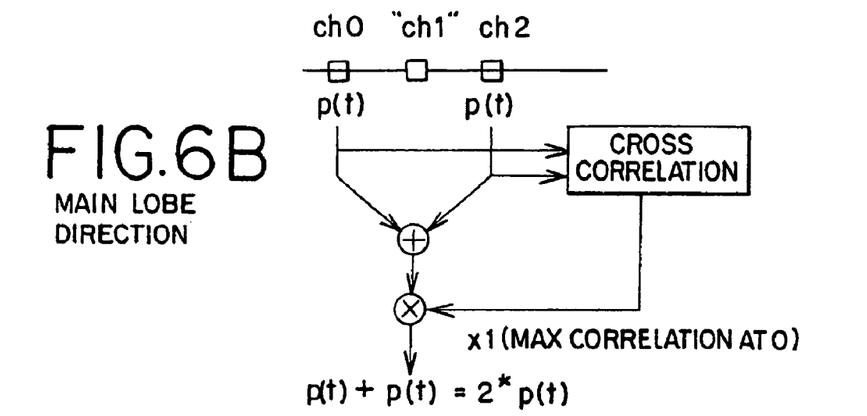
Figure 6C:
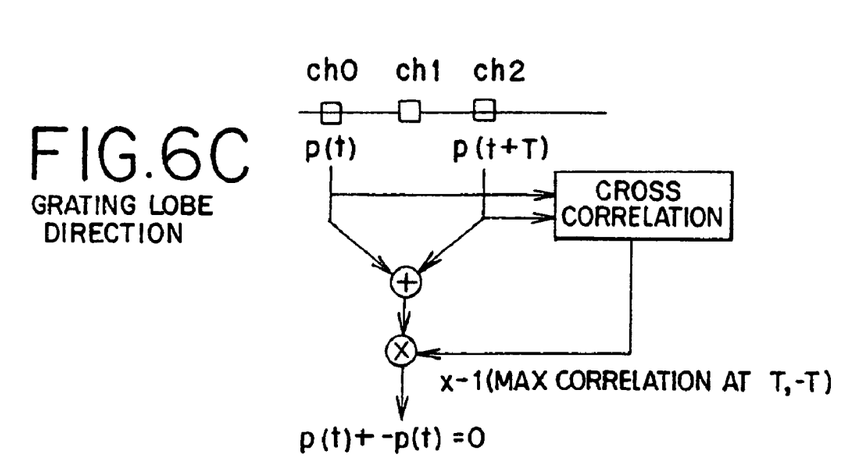

FIGS. 6B and 6C show the beamformation process adapting to the detection of grating lobe clutter. Ultrasound data is acquired after application of beamforming delays and prior to channel summation for detecting or measuring the presence of grating lobe clutter. For example, channel data from adjacent but sparsely spaced elements of a transducer array is acquired for channels 0 and 2. In one embodiment, the sparse spacing is a one-wavelength spacing, but other spacings may be provided. The acquired channel data is used to form data representing a virtual element as well as to determine the presence of grating lobe clutter.

To determine the presence of grating lobe clutter, the signals from the two different transducer elements are correlated. In one embodiment, the coherence factor processor 54 of FIG. 5A determines a normalized cross-correlation of the signals from the two different elements as shown in FIGS. 6B and 6C. Alternatively, other correlation or coherence functions, such as the minimum sum of absolute differences, are used. The coherence between adjacent elements indicates the primary direction of the received energy. Signals over a time period associated with a single range gate location are compared. In one embodiment the signals from the actual elements are filtered before coherence factor processing. For example a band-pass filter suppresses the lower frequency components of the imaging spectrum. Since grating lobes are more likely to be at the higher frequencies, filtering prior to the coherence factor processing improves the grating lobe detection. The filtering can be done in time or frequency domain. A filter bank can be used instead of a single filter. The output of each filter is then processed independently through the coherence factor processor, and through the rest of the signal path that generates the virtual element signals. The same filter can be applied to all channels, or it can be varied from channel to channel. For example, the center frequency of the filter can be shifted as a function of the relative angle between the respective element's normal and the line that connects the element with the focal point.

The coherence factor processor 54 delays the signal from one channel, such as channel 2, relative to the signal of the other channel, such as channel 0, for applying different shifts as part of the peak correlation search. The signals are shifted relative to each other to determine a plurality of correlation parameters. Where a peak correlation or the maximum correlation occurs closer to a time associated with no shift between the signals, the energy is indicated as being principally from the main lobe. Where the peak coherence occurs at a shift of about one period, the energy is principally from the grating lobe. In alternative embodiments, other phase shifts are used to indicate energy principally from the grating lobe, such as a half period shift. The shift is a function of the spacing between the elements. In one embodiment, only two correlation calculations are performed, one associated with no time shift and the other associated with a period time shift. The maximum of the two values indicates whether the energy is principally from the main lobe or the grating lobe. In alternative embodiments, a plurality of correlations associated with various levels of time shift are performed. A threshold is then selected to distinguish one set of shifts as associated with energy from the main lobe from another set of shifts associated with energy from the grating lobe. In an alternative embodiment, three correlation calculations are provided: one for no time shift, one for a positive time shift by a period and one for a negative time shift by a period. A peak correlation or larger correlation value associated with the plus or minus period time shift indicates energy principally from grating lobes direction.

As shown in FIGS. 6B and 6C, the signals representing the virtual elements channel 1 are formed by summing the signals from adjacent elements channel 0 and channel 2. The sum is normalized, resulting in an average signal of a similar amplitude to the signals of the other channels. A weighted sum or interpolation may be used.

The signal representing the virtual element is phased as a function of the grating lobe determination. The phase of the sum is altered as a function of the amount of correlation. As shown in FIG. 6B, the sum is multiplied by a positive one value where the energy is associated with a main lobe direction. Other positive values than one may be used, such as for applying apodization to weight the virtual channel 1 relative to other channels. As shown in FIG. 6C, where the energy is primarily from the grating lobe direction, the sum is multiplied by a negative 1. The negative 1 value may be replaced with a different negative value to apply both the shift and apodization. In alternative embodiments, the apodization is separately applied. The negative 1 value shifts the sum by a 180 degrees and a positive 1 value shifts the sum by 0 degrees or applies no shift. The phase shift is a function of the object field, such that the receive beamformer 16 adaptively forms the virtual element signal to either cancel out energy from the grating lobe or enhance energy from main lobe directions. In alternative embodiments, the phase shift is implemented with a delay or buffer. While a phase shift of 180 degrees or no shift is described above, different shifts may be used for canceling out grating lobe energy or maintaining main lobe energy. Other phase shifts could be formed as an arbitrary function of the coherence value at the main lobe direction, the grating lobe direction, and/or other directions. Other inputs to the processor determining the phase could be the relative or absolute energy levels of the signals. Different shifts are a function of the grating lobe clutter alone or the grating lobe clutter and other considerations, such as additional beamforming delays (in particular the local steering direction of the two real elements) being applied to the virtual element for beamformation. In another alternative embodiment, the coherence processor could apply a gain of 0 to channel pair form by the real and virtual channel when grating lobe energy predominates and a gain of 1 when the main lobe energy predominates. Other gain values between 0 and 1 could be used based on a function with the same parameters as used above for determining a phase adjustment.

The phase of the virtual element is adjusted in real time. As a result, the signal representing the virtual element is available for beamformation with signals from other virtual and actual elements. The delay and apodized signals from both virtual and actual elements are summed together to form beamformed ultrasound data. The beamformed ultrasound data represents a tissue, structure or fluid at a particular location in a scan region.

In one embodiment, the threshold for determining whether energy is principally from the grating lobe versus main lobe direction varies as a function of the type of imaging application for the ultrasound data received. Where a plurality of point targets are being are likely to be imaged, the threshold is adjusted such that energy is more likely to be determined from the main lobe direction. As another example, where the signals indicate speckle without associated tissue or structure, the threshold may adaptively be set to more likely identify energy as from the grating lobe direction.

Using the adaptive beamformer for grating lobe suppression, the data for virtual elements is beamformed with data from actual elements. For every adjacent pair of actual elements used to form a virtual element, beamformed data representing about double the number of elements is provided. Sparse sampling of the array is used without an increased or with minimal increase in grating lobe clutter. In alternative embodiments, signals from non-adjacent, three or more, or any other combination of actual elements are used to form one or more virtual elements.

Using the sparse array, random element spacing, lower frequency operation, harmonic imaging and using different transmit and receive aperture or element configurations are provided while minimizing an increase in grating lobe clutter. The beamformer adaptively rejects grating lobe energy as a function of the object field so that the beamformer sensitivity to the grating lobe direction is adjusted. By adapting the signals for the virtual elements, the virtual elements across an aperture either contribute to the main lobe energy or reduce grating lobe energy. As a result, the effective size of the aperture increases or decreases as a function of the grating lobe clutter. Grating lobe clutter is most likely contributed by the edge elements. Where grating lobe clutter is detected in virtual elements at the edges of the aperture, the virtual element is used to cancel out the grating lobe energy, effectively eliminating or reducing the contribution of elements at the edge of the array. The adaptive process then contributes additional elements throughout the reminder of the array where energy is associated with the main lobe direction. As a result, the maximum aperture size possible given the object field being scanned is adaptively and automatically determined.

In an alternative embodiment of adaptive beamformation, the virtual channels are optional. The similarity between signals from two different transducer elements is determined as discussed above, such as by calculating a correlation or coherence. Where grating lobes information or clutter is detected, a gain of one or both of the transducer elements is decreased or set to zero. For example, the signals used for determining the similarity are set to zero due to high grating lobe content.

Adaptive beamformation for grating lobe suppression may allow for higher frame rate imaging. For example, maximum information beamformation where beamformation using plane wave transmit signals is provided. By adaptively removing grating lobe clutter in the received ultrasound data, the grating lobe effects of using a broad transmit beam are minimized. By reducing scan head electronics or eliminating scan head electronics and allowing sparse sampling, real time four-dimensional imaging may be provided.

The adaptive beamformation and filtering processes are discussed above for a particular location, range, scan line or frame. The acquisition determination of grating lobe level and alteration are performed separately for each of a plurality of locations, range gates, scan lines and/or frames. For example, adaptive beamformation or filtering processes are repeated independently for each sample or range gate location within a scan region. The thresholds, functions used, processes adapted or other feature of the adaptation may vary as a function of location. For example, the threshold applied to indicate the existence of grating lobe clutter and the differences in alternative processing are varied as a function of at least one of steering angle and range location. For example, the determination of the grating lobe clutter is made more likely to not find grating lobe clutter for steep steering angles and/or the combination of input and output filtered data is more likely to select the output filtered data for increasing steering angles. As a result, information is contributed from the increased steering angle without being cancelled while reducing some grating lobe clutter. Since deeper depths are associated with more opportunity for grating lobe clutter, different thresholds may be adapted to more likely detect and alter processing in response to the detection of grating lobe clutter for deeper depths than for narrow depths.

While the invention has been described above by reference to various embodiments, it should be understood that many changes and modifications can be made without departing from the scope of the invention. It is therefore intended that the foregoing detailed description be regarded as illustrative rather than limiting and that it be understood that it is the following claims, including all equivalents, which are intended to define the spirit and scope of this invention.

We claim:

1. A method for adaptive grating lobe suppression in ultrasound processing, the method comprising:
    (a) acquiring ultrasound data;
    (b) determining a grating lobe level as a function of the ultrasound data; and
    (c) altering processing in response to the grating lobe level, further wherein (b) comprises determining similarity of signals from two different transducer elements and (c) comprises altering a phase of a sum of the signals from the two different transducer elements, the altering being a function of an amount of correlation.

2. The method of claim 1 wherein (b) comprises determining whether a peak correlation occurs closer to no shift between the signals from the two different transducer elements than a period shift between the signals from the two different transducer elements, the no shift and period shift being for the signals after application of any beamforming delays.

3. The method of claim 1 wherein (c) comprises selecting one of: shifting the sum by 180 degrees and applying no shift as a function of the amount of correlation.

4. The method of claim 3 wherein (c) comprises multiplying by negative one when the amount of correlation indicates energy from a grating lobe and multiplying by positive one when the amount of correlation indicates energy from a main lobe.

5. The method of claim 1 wherein (a) comprises acquiring the ultrasound data after application of beamforming delays and prior to channel summation, the ultrasound data being channel data.

6. The method of claim 5 wherein (a) comprises acquiring the ultrasound data from a sparse spacing of the two different transducer elements;

further comprising:
(d) forming a virtual element signal as the sum; and
(e) beamforming with the acquired ultrasound data and the virtual element signal.

7. The method of claim 1 wherein (b) comprises determining similarity of signals from two different transducer elements and (c) comprises setting a gain for one of the two different transducer elements as a function of the similarity.

8. The method of claim 7 wherein (c) comprises setting the gain to zero for high grating lobe content.

9. The method of claim 7 wherein (c) comprises setting the gain for both of the two different transducer elements as a function of the similarity.

10. A system for adaptive grating lobe suppression in ultrasound processing, the system comprising:
an ultrasound transducer; and
a processor connected with the ultrasound transducer, the processor operable to determine a level of grating lobe clutter in ultrasound data from the ultrasound transducer and operable to alter processing in response to the level of grating lobe clutter, further
wherein the ultrasound transducer comprises a sparsely sampled array of elements; and
wherein the processor is operable to correlate signals from two different transducer elements and altering a phase of a sum of the signals from the two different transducer elements, the altering being a function of an amount of correlation.

* * * * *